US010349867B2

(12) United States Patent
Bassez et al.

(10) Patent No.: US 10,349,867 B2
(45) Date of Patent: Jul. 16, 2019

(54) DEVICE FOR TAKING A MEASUREMENT

(71) Applicant: LABORATOIRES INNOTHERA, Arcueil (FR)

(72) Inventors: Sophie Bassez, Villebon sur Yvette (FR); Amina Ouchene, Creteil (FR)

(73) Assignee: LABORATOIRES INNOTHERA, Arcueil (FR)

( * ) Notice: Subject to any disclaimer, the term of this patent is extended or adjusted under 35 U.S.C. 154(b) by 103 days.

(21) Appl. No.: 15/626,479

(22) Filed: Jun. 19, 2017

(65) Prior Publication Data
US 2017/0360331 A1 Dec. 21, 2017

(30) Foreign Application Priority Data

Jun. 17, 2016 (FR) .................................... 16 55647

(51) Int. Cl.
G01B 3/10 (2006.01)
A61B 5/107 (2006.01)
A61B 5/00 (2006.01)
B65H 75/40 (2006.01)
G01B 5/02 (2006.01)
G01D 5/12 (2006.01)
G01D 5/347 (2006.01)
A41H 1/02 (2006.01)

(52) U.S. Cl.
CPC ............ *A61B 5/1075* (2013.01); *A61B 5/002* (2013.01); *A61B 5/1072* (2013.01); *A61B 5/742* (2013.01); *A61B 5/7405* (2013.01); *A61B 5/746* (2013.01); *B65H 75/406* (2013.01); *G01B 3/1041* (2013.01); *G01B 3/1061* (2013.01); *G01B 3/1082* (2013.01); *G01B 3/1084* (2013.01); *G01B 5/02* (2013.01); *G01D 5/12* (2013.01); *G01D 5/347* (2013.01); *A41H 1/02* (2013.01); *A61B 5/7221* (2013.01); *G01B 2003/1043* (2013.01); *G01B 2003/1069* (2013.01)

(58) Field of Classification Search
CPC ............................ A61B 5/1075; G01B 3/1041
USPC ............................................ 33/2 A, 759, 763
See application file for complete search history.

(56) References Cited

U.S. PATENT DOCUMENTS

| | | | | |
|---|---|---|---|---|
| 2,129,582 A * | 9/1938 | Johansson | ............ | G01B 3/1084 242/385.4 |
| 3,832,780 A * | 9/1974 | Lewis | ............ | A41H 1/02 33/15 |
| 4,242,574 A * | 12/1980 | Grant | ............ | G01B 3/1061 33/763 |
| 4,502,301 A * | 3/1985 | Swallow | ............ | A61F 13/08 602/62 |
| 4,569,139 A * | 2/1986 | Wakeling | ............ | G01B 5/025 33/555.4 |
| 4,890,392 A * | 1/1990 | Komura | ............ | G01B 3/1061 33/762 |
| 4,896,280 A * | 1/1990 | Phillips | ............ | G01B 3/1061 33/759 |
| 4,899,460 A * | 2/1990 | Kang | ............ | G01B 3/1005 242/381.3 |
| 4,974,331 A * | 12/1990 | Watterson | ............ | A41H 1/02 33/15 |
| 5,142,793 A | 9/1992 | Crane | | |
| 5,193,287 A * | 3/1993 | Coulter | ............ | A61B 5/107 33/511 |
| 5,367,785 A * | 11/1994 | Benarroch | ............ | E05B 67/006 33/755 |
| 5,406,715 A * | 4/1995 | Koizumi | ............ | G01B 3/1002 33/512 |
| 5,433,014 A * | 7/1995 | Falk | ............ | G01B 3/1061 33/755 |
| 5,619,804 A | 4/1997 | Vogt et al. | | |
| 5,891,059 A * | 4/1999 | Anderson | ............ | A61B 5/107 600/561 |
| 5,983,514 A * | 11/1999 | Lindsey | ............ | G01B 3/1061 33/760 |
| 6,070,338 A * | 6/2000 | Garity | ............ | G01B 3/1084 33/42 |
| 8,146,261 B1* | 4/2012 | Perry | ............ | G01B 3/1084 33/511 |
| 2002/0004992 A1* | 1/2002 | Oser | ............ | A61B 5/107 33/555.4 |
| 2002/0088135 A1* | 7/2002 | Arlinsky | ............ | G01B 3/1041 33/760 |

(Continued)

FOREIGN PATENT DOCUMENTS

FR 2788957 A1 8/2000
FR 2788987 A1 8/2000

OTHER PUBLICATIONS

Feb. 28, 2017 Search Report submitted within French Patent Application No. 1655647, (No English translation).

*Primary Examiner* — Christopher W Fulton
(74) *Attorney, Agent, or Firm* — Oliff PLC

(57) ABSTRACT

A device for taking a measurement of a dimension of a part of the body of a patient, includes: an electronic tape measure having a portable housing, a winder accommodated in the housing, a tape which is partially wound on the winder and of which a portion, called the "unwound portion", extends outside the housing, and a measuring module for a measurement, relative to the unwound portion; a consistency control module for checking the consistency of the measurement by at least one consistency rule and at least one context datum; and an alert module for delivering an alert if an inconsistency is detected by the consistency control module.

19 Claims, 1 Drawing Sheet

(56) References Cited

U.S. PATENT DOCUMENTS

| | | | |
|---|---|---|---|
| 2002/0184779 A1* | 12/2002 | Bohnengel | G01B 3/1056 33/555.4 |
| 2004/0040170 A1 | 3/2004 | Sanoner | |
| 2006/0025706 A1* | 2/2006 | Chen | A61B 5/107 600/587 |
| 2008/0270069 A1* | 10/2008 | Cros | G06T 17/20 702/166 |
| 2008/0276477 A1* | 11/2008 | Albrecht | G01B 3/1082 33/707 |
| 2011/0258869 A1* | 10/2011 | Bittkowski | A61B 5/107 33/512 |
| 2014/0196301 A1* | 7/2014 | Towns | A43D 1/02 33/769 |
| 2015/0308807 A1* | 10/2015 | Rhoden | G01B 3/1061 33/763 |

\* cited by examiner

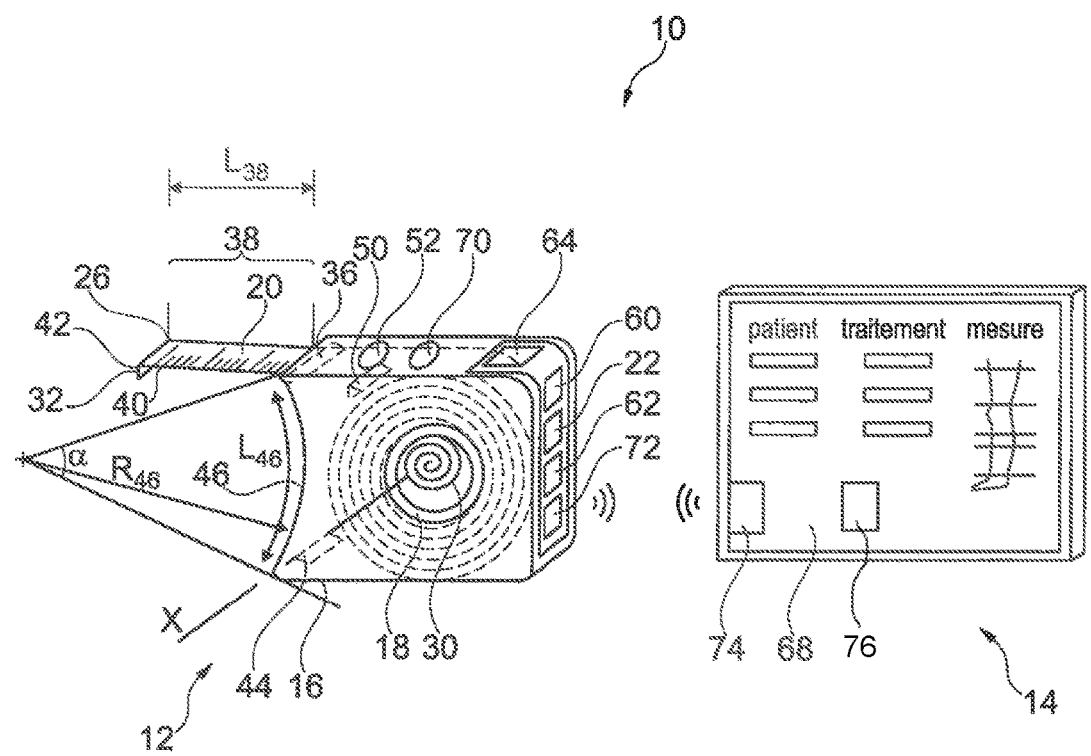

DEVICE FOR TAKING A MEASUREMENT

TECHNICAL FIELD

The invention relates to a device for measuring a dimension of a part of the body of a patient, intended in particular for measuring perimeters of a leg of a patient with a view to prescribing an elastic venous compression orthosis indicated in cases of venous insufficiency of a lower limb of a patient.

PRIOR ART

Elastic venous compression orthoses, formerly known as "retention stockings (or hoses)" or "retention tights", are textile medical devices producing a therapeutic effect through compression of the lower limbs, unlike "support stockings" (or even "support hoses" or "anti-fatigue stockings") and "fashion stockings", which are not medical devices with a therapeutic purpose.

The elastic venous compression orthoses are designed to produce a therapeutic effect through compression of the lower limb over a greater or lesser extent, usually with a pressure profile decreasing upwards from the ankle.

Since the morphology of the lower limbs differs from one patient to another, an orthosis model is conventionally offered in several sizes in order to satisfy the market.

In order to determine the size of an elastic venous compression orthosis intended for a patient, it is necessary to measurer different dimensions of his leg, especially perimeters at different altitudes. In particular, the measurements may be taken at standardized altitudes.

In order to measure a perimeter, a conventional tape measure may be used. However, the quality of the measurement depends on the operator in charge of this measurement.

Reading off the graduation of the tape may also be the source of parallax errors.

The quality of the measurements is particularly important when they are used to choose an orthosis that is adapted to a particular pathology. The efficacy of a treatment is in fact directly dependent on the correct fit of the orthosis to the morphology of the patient.

FR 2 788 957 proposes a device for taking measurements electronically. This device has in particular a coder which is capable of evaluating the unwound length of the tape without intervention by the operator. This device reduces the risk of error.

However, there is always a need to improve the quality of the measurements that are carried out.

An object of the present invention is to respond to this need.

SUMMARY OF THE INVENTION

The invention proposes a device for taking a measurement of a dimension, in particular a perimeter dimension, of a part of the body of a patient, said device having:
- an electronic tape measure having a portable housing, a winder accommodated in the housing, a tape which is partially wound on the winder and of which a portion, called the "unwound portion", extends outside the housing, and a measuring module for a measurement, relative to said unwound portion;
- a consistency control module for checking the consistency of said measurement by means of at least one consistency rule and at least one context datum, and
- an alert module for delivering an alert if an inconsistency is detected by said consistency control module.

As will be seen in more detail in the description below, a device for taking measurements according to the invention not only makes it possible to take a measurement electronically but also to verify that said measurement is compatible with the context in which the device has been used. In particular, in one embodiment, the measuring device makes it possible to verify that the measurement is compatible with the treatment applied and/or with measurements carried out previously.

A device according to the invention may also comprise one or more of the following preferred optional features:
- said measurement is a function of the length of the unwound portion and/or a tension of the unwound portion and/or a position of the housing and/or a position of the unwound portion, in particular an attitude of the housing;
- said at least one context datum comprises at least one datum specific to the taking of said measurement, called the "specific context datum";
- said at least one specific context datum is:
  - a personal datum relating to the patient, and/or
  - a therapeutic datum relating to a treatment applied to the patient, and/or
  - a measurement datum relating to the nature of the measurement, and/or
  - a history datum relating to a measurement taken previously, for the patient or another patient similar to the patient and/or a patient having undergone an identical treatment, and/or preferably relating to a measurement of the same nature;
- the consistency rule evaluates the compatibility of the measurement with a range of lengths and/or altitudes and/or attitudes and/or tensions, and/or the compatibility of the instant of the measurement with a time interval, preferably determined as a function of the context data;
- the consistency control module is configured to evaluate the origin and/or the degree of an inconsistency and/or to evaluate the deviation of the measurement from a reference value;
- the device has an interface permitting selection and/or entry of at least one context datum by an operator and/or selection and/or entry of at least one consistency rule by an operator;
- the consistency control module and/or the alert module are arranged in the housing; alternatively, the device has a base separate from the tape measure, preferably a computer, a tablet or a telephone, the consistency control module and/or the alert module being arranged in said base, the base and the tape measure having respective communication means adapted for communication, preferably radio communication, between said base and said tape measure;
- the base and the tape measure are able to communicate said measurement and/or an alert generated by the alert module and/or a context datum and/or a consistency rule;
- the base has an analysis module configured to determine a size of orthosis, said determination depending on said measurement if the consistency control module has not detected inconsistency relating to said measurement;
- the tape measure has:
  - a pawl which may preferably be manually deactivated, permitting the rotation of the winder in the direction of unwinding of the tape and, depending on whether the pawl is activated or deactivated, prohibiting or permitting, respectively, the rotation of the winder in the direction of winding of the tape, a spring tending to turn the winder in the direction of winding, and a fastener arranged at the free end of the tape and designed for fixing to a fastener region of the housing;

said fastener is magnetic;

the device has a concave bearing surface, of which the radius of curvature is, at each point of said bearing surface, between 2.0 and 15 cm, preferably between 2.5 and 15 cm;

the housing has a slit from which said unwound portion emerges, the slit opening out in immediate proximity to the bearing surface or in the bearing surface, the fastener region being arranged opposite the slit with respect to the bearing surface;

the tape is made of a hypoallergenic material.

The invention also relates to a method for taking a measurement of a dimension of a part of a body of a patient by means of a device according to the invention. The method preferably has the following steps:

a) placing the housing on said part of the body;

b) partially unwinding the tape and, if said dimension is a perimeter dimension, fixing the free end of the tape to the fastener region of the housing;

c) deactivating the pawl, in such a way as to place the tape flat on said part of the body of the patient, under the effect of the spring;

d) triggering a measurement;

e) independently of steps a) to d), but before step f), entering and/or selecting at least one specific context datum;

f) using said consistency control module to check the consistency of the measurement with said specific context datum;

g) alert, by said alert module, in the case of inconsistency, preferably specifying the origin and/or the degree of the inconsistency;

h) repeating at least steps a) to d) and f) and g) in the case of an alert.

If the dimension is a perimeter dimension, then, in step a), a concave bearing surface of the housing is preferably placed on said part of the body, preferably transversely with respect to the general direction of said part of the body of the patient (the axis of a leg, for example).

The invention finally relates to a method for determining a size of an elastic venous compression orthosis, said method having the following successive steps:

A) taking a set of measurements using a method for taking measurements according to the invention, the set of measurements preferably including at least one measurement of a calf perimeter and of an ankle perimeter;

B) choosing an orthosis size corresponding to said set of measurements, depending on a therapeutic treatment that is to be applied.

Preferably, said set of measurements includes a measurement of the length of the leg or crotch.

Also preferably, the base of the tape measure has an analysis module configured to determine said size as a function of said set of measurements.

DEFINITIONS

"Altitude" or "level" corresponds to a level in the vertical direction when the orthosis is worn by a patient standing up straight, as shown in FIG. 7 of the French standard NF G 30-102, part B, which shows a leg model of the Hohenstein type.

"Tape" is understood in the conventional sense as a long and narrow band. In the present description, a "tape" also includes a wire.

A "patient" is not limited to humans and instead includes any animal.

BRIEF DESCRIPTION OF THE FIGURES

Other features and advantages of the invention will become clearer from reading the following detailed description and from examining the attached drawing, in which FIG. 1 shows a schematic representation of a device according to the invention.

DETAILED DESCRIPTION

FIG. 1 shows a schematic representation of a device 10 according to the invention for taking measurements, having a portable electronic tape measure 12 and a base 14 at a distance from the tape measure.

The tape measure 12 conventionally has a housing 16, a winder 18 accommodated in the housing, a tape 20 partially wound up on the winder 18, and a measuring module 22.

The tape 20 is intended to go round a part of the body of a patient in order to measure a perimeter dimension. This part of the body may be in particular an upper limb or a lower limb, in particular a lower limb. For better precision, the tape may in particular be placed in contact with the skin of the patient. It is preferably made of a hypoallergenic material.

The tape 20 preferably has a width of more than 1 cm, preferably more than 2 cm and/or less than 5 cm, less than 4 cm, less than 3 cm, and/or a thickness of less than 1 mm, preferably less than 0.5 mm, preferably less than 0.3 mm, and/or a length of more than 1 m, preferably more than 1.3 m and/or less than 2 m, preferably less than 1.7 m, with a length of 1.5 m being especially suitable. The width and/or the thickness of the tape are preferably constant.

The winder 18 is traditionally in the general form of a drum that is movable in rotation about its axis X. A first end of the tape 20 is fixed to the cylindrical lateral surface of the winder. The second end, or "free end" 26, of the tape 20 is free and extends outside the housing. A spring 30 tends to turn the winder 18 in a first direction, called the "winding direction". The opposite direction is called the "unwinding direction".

In a position called the "rest position", almost the entire tape 20 is wound up on the winder, with only the free end 26 of the tape 20 extending outside the housing. Traditionally, the free end 26 has a stop 32 which, in the rest position, bears on the rim of a slit 36 which is formed in the housing 16 and through which the tape 20 passes.

The unwinding of the tape 20 is traditionally effected by pulling its free end 26 counter to the moment exerted on the winder 18 by the spring 30. The portion of the tape 20 extending outside the housing is called the "unwound portion".

In contrast to a mechanical tape measure, the electronic tape measure 12 also has a measuring module 22 for electronically determining a measurement M.

The measuring module 22 may, for example, have a coder for the rotation of the winder 18 or a coder, for example an optical or magnetic coder, detecting and counting marks 40 of the tape 20 that pass in front of it, as is described in FR 2 788 957, in order to evaluate the length $L_{38}$ of the unwound portion 38.

Preferably, the marks 40 are graduations, for example in centimeters or in inches. Advantageously, the operator may thus evaluate approximately the length of the unwound portion by simply reading off the graduations and, if appropriate, may verify that the electronic measurement provided by the tape measure is compatible with what he sees.

The free end of the tape 20 preferably has a fastener 42 for temporarily fixing to the housing. Here, "temporarily" means that the fastener may be deactivated by a simple manipulation. Preferably, the fastener allows the free end of the tape to be fixed only to a limited part of the housing called the "fastener region" 44. The fastener region preferably has a surface area of less than 2 cm², preferably of less than 1 cm².

The nature of the fastener 42 is not limited. For example, the fastener may be in the form of a clip or a pin, with the fastener region being configured accordingly. The fastener is preferably magnetic, with the fastener region being made of a ferrous material.

Also preferably, the fastener 42 serves as a stop 32.

Between the slit 36 and the fastener region 44, the housing 16 preferably defines a bearing surface 46, which is preferably substantially cylindrical. Preferably, the radius of curvature $R_{46}$ of the bearing surface 46 is, at each point, between 2.0 and 15 cm, preferably between 2.5 and 15 cm. Preferably, the radius of curvature $R_{46}$ is substantially constant, regardless of the point of the bearing surface 46 considered.

Preferably, the bearing surface 46 extends angularly, preferably over an angle sector α of greater than 20 degrees, preferably greater than 30 degrees, preferably greater than 50 degrees, preferably greater than 60 degrees, and/or less than 90 degrees, preferably less than 80 degrees, preferably less than 70 degrees.

The width of the bearing surface 46, measured along the axis X, is preferably more than 1 cm, and/or less than 5 cm, 4 cm, 3 cm or 2 cm. Preferably, the width of the bearing surface 46 is greater than the width of the tape, preferably more than 1.05 times the width of the tape, and/or preferably less than twice, preferably less than 1.5 times, preferably less than 1.2 times the width of the tape. Preferably, the width of the bearing surface 46 is substantially constant.

Also preferably, the fastener 42 is configured in such a way that, in the fastened position of the tape, in which the fastener 42 is fixed to the fastener region, the tape is able to continue the bearing surface 46 substantially without discontinuity of slope. Preferably, the slit 36 is formed on the bearing surface 46, preferably at an end of the bearing surface 46. Advantageously, the precision of the measurement is thereby improved. Patient comfort is also enhanced.

The median longitudinal plane of the bearing surface 46 and/or the median transverse plane of the winder 18 and/or the median longitudinal plane of the tape 20, which are perpendicular to the axis X, are preferably coincident.

Preferably, the tape measure 12 also has means for blocking the partially unwound tape in position, regardless of the degree of unwinding. In a preferred embodiment, these means have a pawl 50 permitting the rotation of the winder in the direction of unwinding and, depending on whether the pawl is activated or deactivated, prohibiting or permitting, respectively, the rotation of the winder 18 in the direction of winding. Preferably, the pawl 50 is activated by default. Preferably, it may be deactivated manually, preferably by pressing a deactivation button 52. After the free end 26 of the tape 20 has been fastened by the fastener 42 to the fastener region 44, the deactivation of the pawl 50 advantageously makes it possible to place the tape 20 flat against the body of the patient under the effect of the spring 30. Advantageously, the precision of the measurement is thereby improved.

In one embodiment, the tape measure also has a tension sensor 64 for measuring the tension on the unwound portion 38.

According to the invention, the device 10 for taking a measurement also has a consistency control module 60 and an alert module 62.

The consistency control module 60 is intended to ensure the quality of the measurement M determined by the measuring module 22. More precisely, the consistency control module 60 processes the measurement M in order to verify the compatibility of the latter with one or more context data C, according to one or more consistency rules R.

The measurement M may be in particular the length $L_{38}$ of the unwound portion or a function of this length, for example the sum of the length $L_{38}$ and of the length $L_{46}$ of the bearing surface 46.

The measurement M may also be, for example, a measurement relating to the position of the tape measure 12, for example the attitude of the unwound portion. The attitude of the unwound portion is the angle between the general plane in which the unwound portion extends and a horizontal plane. The attitude may be evaluated with a level, for example. For measurements relating to a lower limb, in particular in the context of prescribing an elastic venous compression orthosis, the patient may be asked to stand upright during the measurements.

The measurement M may also be a measurement of the tension $T_{38}$ of the unwound portion 38 measured with the tension sensor 64. The measurement M may also be a set of several of the abovementioned measurements, for example the sum of the lengths $L_{38}$ and $L_{46}$ and the tension $T_{38}$.

Preferably, the measurement M is time-stamped.

The context data may comprise general context data and specific context data.

The general context data are data associated with the application in which the device 10 for taking measurements is intended to be used, independently of its specific use for the patient.

Preferably, the context data include specific context data relating to a particular use of the device 10 for taking measurements.

For example, the measuring device may be provided for measuring perimeters of the leg at several reference altitudes with a view to prescribing an elastic venous compression orthosis. In such an application, whoever the patient, a measurement M has to belong to an acceptable range of measurements. This acceptable range of measurements is one example of general context data.

The specific context data may in particular comprise:
personal data relating to the patient, for example a size, the age or the sex of the patient,
therapeutic data relating to a treatment applied to the patient, for example a planned frequency of the measurements, depending on their nature, or a planned development for the measurement of a perimeter,
measurement data relating to the nature of the measurement, in particular an altitude, for example along the leg, and/or relating to an attitude of the housing and/or relating to an instant at which the measurement has to be performed.

The consistency rules make it possible to test the compatibility of the measurement M with the context data, in particular the specific context data.

A consistency rule makes it possible in particular to verify that the measurement belongs to a range determined as a function of at least one specific context datum.

A consistency rule preferably compares the length $L_{38}$, or $L_{38}+L_{46}$, with a range of acceptable lengths, said range preferably being determined as a function of personal data and/or therapeutic data and/or measurement data, and, if the length does not belong to this range, considers this to be an inconsistency.

A consistency rule makes it possible, for example, to verify if the attitude of the unwound portion 38 and/or the tension of the unwound portion 38 is compatible with the conditions planned for the nature of the measurement.

A consistency rule also makes it possible to verify if the measurement M is compatible with another measurement carried out previously (historical measurement), preferably for the same patient or for a similar patient.

A consistency rule also makes it possible to verify if the measurement M, or a development of the measured datum, is compatible with the treatment applied to the patient (therapeutic data).

Preferably, a consistency rule verifies if the instant of the measurement M is compatible with a time interval predetermined for this measurement, for example as a function of the treatment applied to the patient and/or one or more measurements performed previously (historical data).

In a preferred embodiment, the consistency control module 60 is able to detect an inconsistency in the measurement but is also able to evaluate the origin of an inconsistency and/or to quantify the degree of said inconsistency, for example by calculating a deviation between the measurement, or a function of the measurement, and a reference value, which is preferably determined as a function of context data, in particular specific context data.

The alert module 62 is intended to transmit to the operator and/or to the base 14 information relating to the consistency control performed by the consistency control module 60.

The alert module 62 may deliver an alert A in the case of inconsistency, but also preferably additional information I on the origin of the inconsistency and/or on the degree of the inconsistency. For example, the alert module 62 may indicate that the detected inconsistency lies in the incompatibility of the measurement M with a historical measurement or with the altitude at which the measurement M was carried out. Preferably, the alert module 62 specifies, for example, the deviation of the measurement M from a reference value that is considered normal.

The consistency control module 60 and/or the alert module 62 may be arranged inside the housing 16.

In one embodiment, the consistency control module and/or the alert module are arranged in the base 14. The base may be stationary, traditionally a computer, or mobile, for example a telephone or a tablet provided with a suitable app. The use of a smartphone is preferred.

The tape measure 12 and the base 14 have communication modules 72 and 74, respectively. The communication modules are preferably designed for radio transmission of information. The information exchanged between the tape measure 12 and the base 14 may in particular comprise said measurement M and/or an alert A and/or additional information I generated by the alert module and/or a context datum and/or a consistency rule allowing the consistency module to evaluate said measurement.

The integration of the control module and of the alert module in the stationary base 14 advantageously makes it possible to reduce the overall size of the tape measure 12 and, therefore, to make it easier to manipulate when taking a measurement.

Preferably, the device 10 for taking measurements also has an interface 68, for example a keyboard and/or a button and/or a screen, for example a touch screen, allowing the operator to enter one or more context data. In particular, the interface 68 is preferably configured to permit selection of the nature of the measurement, for example to specify a measurement of the ankle, calf or thigh, and/or a selection of data relating to the patient and/or to his treatment.

The location of the interface 68 is not limited. The interface 68 may be on the tape measure, on the base 14, or partly on the tape measure and partly on the base.

Preferably, the measuring device 10 also has a trigger 70, for example in the form of a button, allowing the operator to fix the instant at which the measurement is taken. In particular, the operator may only trigger the measurement after placing the tape 20 around the limb of the patient, fixing the fastener 42 to the fastener region 44 and and then deactivating the pawl 50. In one embodiment, the measurement is triggered automatically, for example as a function of the tension $T_{38}$ or, for example, after the fastener 42 has been fastened and the pawl 50 deactivated.

In the absence of inconsistency, the measurement M is considered to be "validated". It is preferably displayed on the interface 68 and/or recorded.

In a preferred embodiment, the operator may record several validated measurements M in order to compile a set of measurements that is adapted to the selection of of a size of orthosis. The first and last measurements of such a set may be identified, for example, by pressing longer on the trigger 70, for example for more than one second.

In a preferred embodiment, the device 10 for taking a measurement also has an analysis module 76 configured to determine at least one orthosis size adapted to said set of measurements.

The analysis module 76 therefore has means for communication with the consistency control module in order to receive the validated measurements M.

Preferably, the analysis module 76 is in the tape measure or in the base, depending on whether the consistency control module is in the tape measure or in the base, respectively. A physical communication, for example by wire or by conductor tracks, is then possible.

The analysis module 76 may be activated, for example, after receipt of a last measurement, without intervention by the operator.

The size determined by the analysis module 76 may be displayed, for example, on the interface 68. Of course, the analysis module 76 then has means of communication with the interface 68.

The manufacture of a measuring device according to the invention does not pose any particular difficulty. In particular, the electronic modules, such as the consistency control module and the alert module, or the communication modules may be easily manufactured by means of conventional electronic tools, in particular including a processor, a data memory and software. The software conventionally includes code instructions, making it possible to obtain the desired functions when these instructions are executed by the processor.

The way in which the device 10 for taking measurements functions may be derived directly from the above description.

To carry out a measurement of a perimeter dimension, the operator may proceed as follows:

At step a), he places the bearing surface 46 on the corresponding part of the body, for example on a leg of the patient. He orients the tape measure depending on the dimension that is to be measured. For example, in order to measure the perimeter of the calf, he orients the housing substantially transversely with respect to the direction of the leg.

At step b), he pulls on the free end 26 of the tape, which emerges from the slit 36 of the housing, in such a way as to unwind a portion of the tape with a length sufficient to go round the leg and to fasten the fastener 42 to the fastener region 44 of the housing.

During this procedure, the pawl 50 prohibits any winding of the tape 20 on the winder under the effect the spring 30.

Generally, the length of the unwound portion 38 which protrudes from the housing is greater than the length that is strictly necessary for going round the leg.

At step c), the operator acts on the deactivation button 52 which deactivates the pawl 50 and thus permits winding of the tape, under the effect of the spring 30, until the unwound portion bears tightly on the surface of the leg.

At step d), the operator triggers the measurement by pressing on the trigger 70.

At step e), independently of steps a) to d), but before step f) described below, a context datum is recorded, for example input by the operator.

Preferably, at least one consistency rule tested by the consistency control module 60 uses a specific context datum. In particular, it is advantageous to use historical data relating to the patient, in particular historical measurements relating to measurements of the same nature, for example relating, like the measurement M, to a perimeter of the calf, and/or relating to the same patient. In this case in particular, no context datum has be be entered by the operator.

The operator may, for example, enter the altitude of the measurement, or an identification of the patient, for example by means of a touch screen (interface 68), preferably on the base 14. The location of the interface 68 is not limited.

A context datum may be entered in the measuring device by way of the stationary base 14 and/or by way of the tape measure 12. Some of the context data may be entered by way of the tape measure and some by way of the base. For example, it may be expedient to enter the altitude of the measurement by means of the tape measure 12, as described in FR 2 788 987, and to enter the identifier or personal data of the patient in the base.

In a preferred embodiment, the consistency control module is integrated in the base. The communication module of the tape measure 12 then communicates the measurement to the base. The consistency module may then process this measurement by means of a consistency rule and may optionally detect an inconsistency.

In the case of inconsistency, the consistency control module transmits corresponding information to the alert module 62 such that the latter warns the operator.

At step f), the alert module sends the operator an alert A and/or additional information I in order to signal any inconsistency, preferably specifying the origin and/or the degree of the inconsistency.

Preferably, the alert module is integrated in the tape measure 12. The operator may thus immediately repeat a measurement taking the alert into account.

The alert may in particular be a sound or a light. For example, the tape measure may emit a beep and/or cause a red diode to flash.

At step h), the operator repeats the measurement if an inconsistency has been detected.

The method for taking a measurement is preferably used to determine a size of elastic venous compression orthosis.

At step A), steps a) to h) described above are carried out several times in order to compile a set of measurements at altitudes, or "reference levels", that are appropriate for the choice of a size.

Preferably, the set of measurements includes at least one measurement of an ankle perimeter and a measurement of a calf perimeter, and preferably a measurement of a thigh perimeter and/or of a hip perimeter.

In a preferred embodiment, the device according to the invention is also used to measure the length of a leg or crotch.

At step B), the doctor or the pharmacist may choose a size corresponding to said set of measurements, conventionally by means of a grid.

In a preferred embodiment, the size is determined by the analysis module as a function of said set of measurements. Preferably, the analysis module is integrated in the tape measure or, preferably, in the base. The analysis module preferably proposes a size automatically, that is to say without particular intervention of the operator, except possibly to initiate analysis software in said analysis module.

As will be clear from the above, the invention provides means by which the quality of the measurements of perimeter dimensions may be improved, which leads to an improved quality of the treatment that is applied.

Of course, the invention is not limited to the embodiments that have been described and shown for illustrative and non-limiting purposes.

In particular, a device according to the invention may also be used to measure dimensions different than a perimeter dimension, for example the length of a leg.

The invention claimed is:

1. Device for taking a measurement of a dimension of a part of the body of a patient, the device having:
   an electronic tape measure having a portable housing, a winder accommodated in the housing, a tape which is partially wound on the winder and of which a portion, called the "unwound portion", extends outside the housing, and a measuring module for a measurement, relative to the unwound portion;
   a consistency control module for checking the consistency of the measurement by means of at least one consistency rule and at least one context datum, and
   an alert module for delivering an alert if an inconsistency is detected by the consistency control module.

2. Device according to claim 1, in which the measurement is a function of the length of the unwound portion and/or a tension of the unwound portion, and/or a position of the housing and/or a position of the unwound portion.

3. Device according to claim 1, in which the at least one context datum comprises at least one datum specific to the taking of the measurement, called the "specific context datum", chosen from among:
   a personal datum relating to the patient and/or a therapeutic datum relating to a treatment applied to the patient, and/or
   a measurement datum relating to the nature of the measurement, and/or
   a history datum relating to a measurement taken previously, for the patient or another similar patient and/or a patient having undergone an identical treatment, and/or relating to a measurement of the same nature.

4. Device according to claim 1, in which the consistency rule verifies that the measurement belongs to a range determined as a function of at least one specific context datum.

5. Device according to claim 1, in which the consistency rule evaluates the compatibility of the measurement with a range of lengths and/or altitudes and/or attitudes and/or tensions, and/or the compatibility of the instant of the measurement with a time interval.

6. Device according to claim 1, in which the consistency control module is configured to evaluate the origin and/or the degree of an inconsistency and/or to evaluate the deviation of the measurement from a reference value.

7. Device according to claim 1, having an interface permitting selection and/or entry of at least one context datum by an operator and/or selection and/or entry of at least one consistency rule by an operator.

8. Device according to claim 1, in which the consistency control module and/or the alert module are arranged in the housing.

9. Device according to claim 1, having a base separate from the tape measure, the consistency control module and/or the alert module being arranged in the base, the base and the tape measure having respective communication means adapted for radio communication between the base and the tape measure.

10. Device according to claim 9, in which the base is a computer, a telephone or a tablet.

11. Device according to claim 9, in which the base has an analysis module configured to determine a size, the determination depending on the measurement if the consistency control module has not detected inconsistency relating to the measurement.

12. Device according to claim 1, in which the tape measure has:
   a pawl which may be manually deactivated, permitting the rotation of the winder in the direction of unwinding of the tape and, depending on whether the pawl is activated or deactivated, prohibiting or permitting, respectively, the rotation of the winder in the direction of winding of the tape,
   a spring tending to turn the winder in the direction of winding, and
   a fastener arranged at the free end of the tape and designed for fixing to a fastener region of the housing.

13. Device according to claim 12, in which the fastener is magnetic.

14. Device according to claim 12, having a concave bearing surface, and in which the housing has a slit from which the unwound portion emerges, the slit opening out in immediate proximity to the bearing surface or in the bearing surface, the fastener region being arranged opposite the slit with respect to the bearing surface.

15. Method for taking a measurement of a dimension of a part of a body of a patient by means of a device according to claim 1, having a concave bearing surface, and in which the tape measure has:
   a pawl which may be manually deactivated, permitting the rotation of the winder in the direction of unwinding of the tape and, depending on whether the pawl is activated or deactivated, prohibiting or permitting, respectively, the rotation of the winder in the direction of winding of the tape,
   a spring tending to turn the winder in the direction of winding,
   a fastener arranged at the free end of the tape and designed for fixing to a fastener region of the housing; and
   in which the housing has a slit from which the unwound portion emerges, the slit opening out in immediate proximity to the bearing surface or in the bearing surface, the fastener region being arranged opposite the slit with respect to the bearing surface;
   the method having the following steps:
   a) placing the housing on the part of the body;
   b) partially unwinding the tape and, if the dimension is a perimeter dimension, fixing the free end of the tape to the fastener region of the housing;
   c) deactivating the pawl, in such a way as to tension the tape under the effect of the spring;
   d) triggering a measurement;
   e) independently of steps a) to d), but before step f), entering and/or selecting at least one specific context datum;
   f) using the consistency control module to check the consistency of the measurement with the context datum;
   g) alert, by the alert module, in the case of inconsistency;
   h) repeating at least steps a) to d) and f) and g) in the case of an alert.

16. Method for taking a measurement of a dimension according to claim 15, in which the dimension is a perimeter dimension.

17. Method for determining a size of an elastic venous compression orthosis, the method having the following successive steps:
   A) taking a set of measurements using a method for taking a measurement according to claim 15, the set of measurements including at least one measurement of a calf perimeter and of an ankle perimeter;
   B) choosing an orthosis size corresponding to the set of measurements, depending on a therapeutic treatment that is to be applied.

18. Method for determining a size of an elastic venous compression orthosis according to claim 17, in which the set of measurements includes a measurement of the length of the leg or crotch.

19. Method for determining a size of an elastic venous compression orthosis according to claim 17, in which the base or the tape measure has an analysis module configured to determine the size as a function of the set of measurements.

* * * * *